United States Patent [19]

Murphy et al.

[11] Patent Number: 5,379,776
[45] Date of Patent: Jan. 10, 1995

[54] HEART RHYTHM CLASSIFICATION METHOD, AND IMPLANTABLE DUAL CHAMBER CARDIOVERTER/DEFIBRILLATOR EMPLOYING THE SAME

[75] Inventors: Anthony J. Murphy, Annandale; David Bassin, Coogee; David Mason, Kilsyth, all of Australia

[73] Assignee: Telectronics Pacing Systems, Inc., Englewood, Colo.

[21] Appl. No.: 160,512

[22] Filed: Dec. 1, 1993

[30] Foreign Application Priority Data

Apr. 1, 1993 [AU] Australia ............... PL8102

[51] Int. Cl.$^6$ .................................... A61B 5/0452
[52] U.S. Cl. .................. 128/705; 128/702; 607/5
[58] Field of Search ........... 607/4, 5; 128/702, 705

[56] References Cited

U.S. PATENT DOCUMENTS

| | | |
|---|---|---|
| 4,475,551 | 10/1984 | Langer et al. |
| 4,799,493 | 1/1989 | DuFault ............... 128/705 |
| 4,830,006 | 5/1989 | Haluska et al. |
| 4,860,749 | 8/1989 | Lehmann |
| 4,875,483 | 10/1989 | Vollmann et al. |
| 5,000,189 | 3/1991 | Throne et al. ............ 128/702 |
| 5,086,772 | 2/1992 | Larnard et al. |
| 5,280,792 | 1/1994 | Leong et al. ............ 128/702 |

FOREIGN PATENT DOCUMENTS

| | | | |
|---|---|---|---|
| 69817A2 | 2/1992 | European Pat. Off. ...... A61N 1/362 |
| WO9209331 | 6/1992 | WIPO ............... A61N 1/368 |

OTHER PUBLICATIONS

Automatic Tachycardia Recognition (Robert Arzbaecher, Thomas Bump, Janice Jenkins, Katherine Glick, Fran Munkenbeck, Jeffrey Brown, N. Nandhakumar) *Pace*, vol. 7, (II) pp. 541–547, May–Jun. 1984.

Tachycardia Recognition by Implantable Electronic Devices (A. John Camm, D. Wyn Davies, David E. Ward) *Pace*, vol. 10 pp. 1175–1190, Sep.–Oct. 1987.

Computer Diagnosis of Supraventricular and Ventricular Arrhythmias: A New Esophageal Technique (Janice M. Jenkins, Delon Wu, Robert C. Arzbaecher) *Circulation* vol. 60, No. 5, pp. 977–987, Nov. 1979.

Tachycardia Differentiation Using One Atrial and Two Ventricular Electrodes (A. D. Mercardo et al.) *Pace*, vol. 10(II) p. 415 (Abstract) 1987.

*Primary Examiner*—William E. Kamm
*Assistant Examiner*—Scott M. Getzow
*Attorney, Agent, or Firm*—Gottlieb, Rackman & Reisman

[57] ABSTRACT

An implantable dual chamber ICD and method senses atrial (A-A) and ventricular (V-V) intervals, calculates the ratio (A/V interval ratio) of A-A intervals to V-V intervals, classifies heart rhythms with V-V intervals (i) above a revert rate threshold as not tachycardia, (ii) below a high rate threshold as treatable tachycardia, (iii) between the two thresholds and below an A-dominant A/V interval ratio threshold as a non-treatable tachycardia, (iv) between the revert rate threshold and the high rate threshold and above a V-dominant threshold as treatable tachycardia and, when the heart rhythm is intermediate all four thresholds, (v) utilizes one or a combination of advanced discriminators (e.g., ventricular windowing, ventricular interval variability, sudden onset, AV-delay creep, ventricular electrogram morphology, active sensing, minute ventilation, or right ventricular pressure) to classify whether the heart rhythm is a non-treatable or a treatable tachycardia.

8 Claims, 5 Drawing Sheets

HEART RHYTHM CLASSIFICATION METHOD, AND IMPLANTABLE DUAL CHAMBER CARDIOVERTER/DEFIBRILLATOR EMPLOYING THE SAME

FIELD OF THE INVENTION

This invention relates to a heart rhythm classification method, and to an implantable cardioverter/defibrillator employing the same.

BACKGROUND OF THE INVENTION

Conventional implantable cardioverter/defibrillators (ICDs) generally employ heart rate rhythm information alone to classify cardiac rhythms. U.S. Pat. No. 4,475,551 to A. A. Langer et al., entitled "Arrhythmia Detection and Defibrillation System and Method," which issued on Oct. 9, 1984, is an example of such a conventional ICD. However, there are rhythms, for example atrial fibrillation (AF) and sinus tachycardia (ST), that can cause a raised ventricular rate but that should not be treated. Thus, the use of rate only rhythm classification is not fully effective.

Similarly, rhythm discrimination in conventional ICDs is less than fully effective due to the fact that, in addition to employing rate-only rhythm classification, such ICDs employ ventricular sensing alone, rather than dual chamber sensing. In the case of ventricular-chamber-only sensing, supraventricular tachycardias are largely ignored, while any rhythm that causes a fast ventricular rate will be treated by the ICD.

Accordingly, rhythms sensed by these ICDs are thus classified as either tachycardia or not tachycardia, and therapy is applied to all tachycardia rhythms. Another example of such existing ICDs is disclosed in U.S. Pat. No. 4,830,006 to E. A. Haluska et al., entitled "Implantable Cardiac Stimulator for Detection and Treatment of Ventricular Arrhythmias" which issued on May 16, 1989. The Haluska et al. patent also employs sudden onset and rate stability in connection with its rhythm classification.

The Haluska et al. simple rate-based classifier has high sensitivity to ventricular tachycardia (VT) and ventricular fibrillation (VF), if programmed correctly. This is achieved, however, at the expense of specificity in the face of sinus tachycardia, atrial fibrillation and atrial flutter. A more advanced system should maintain the sensitivity of the simple system, while providing a substantial improvement in specificity.

The sudden onset algorithm may be useful in patients who have a sinus tachycardia/ventricular tachycardia (ST/VT) rate overlap (i.e., they have a VT which is slower than the maximum heart rate that they can achieve by exercise). There is a real concern, however, that this will compromise the sensitivity to VT as some VTs are very variable and thus may not satisfy the onset criterion. Also, it is common for VTs to be initiated by exercise. Onset has the potential to miss VTs that are initiated from an already elevated sinus rate.

Atrial fibrillation will in many cases cause a high (and usually variable) ventricular rate. A stability test may help in classifying this rhythm but, again, it risks compromising sensitivity (some VTs and most VFs display a highly unstable ventricular rate.) All of the foregoing factors lead to the conclusion that single-chamber rhythm classification has many disadvantages.

U.S. Pat. No. 4,860,749 to M. H. Lehmann, entitled "Tachycardia Detection for Automatic Implantable Cardioverter/Defibrillator With Atrial and Ventricular Sensing Capability" which issued on Aug. 29, 1989, discloses a dual-chamber hierarchical rhythm classification system which includes the following tests in connection with classifying heart rate rhythms:

1. Is the ventricular interval less than some threshold?
2. Is the ventricular interval less than the atrial interval?
3. Is the ventricular interval equal to the atrial interval?
4. Is the atrioventricular interval constant?
5. Is the ventricular interval constant?
6. Is the atrioventricular interval shorter than the predetermined sinus atrioventricular interval?

The above-cited Lehmann patent thus employs a decision tree that is based on the timings of atrial and ventricular intervals. However, it does not describe algorithms for performing any of the rhythm classification tests. Similar, earlier, disclosures of related rhythm classification systems, in which the ventricular interval is compared to a threshold, or to the atrial interval, appear in an article by R. Arzbaecher et al., entitled "Automatic Tachycardia Recognition", appearing in *PACE*, Vol. 7(II), pages 541-547 (May-June, 1984) and in an article by A. J. Camm et al., entitled "Tachycardia Recognition by Implantable Electronic Devices" appearing in *PACE*, Vol. 10, pages 1175-1190 (1987).

The use of the atrioventricular (A-V) interval for rhythm classification was described in an article by J. Jenkins et al., entitled "Computer Diagnosis of Supraventricular and Ventricular Arrhythmias: A New Esophogeal Technique" appearing in *Circulation*, Vol 60(5), pages 977-985 (1979); in the aforementioned A. J. Camm et al. article; and in an abstract by A. D. Mercando et al., entitled "Tachycardia Differentiation Using One Atrial and Two Ventricular Electrodes", appearing in *PACE*, Vol. 10(II), page 415 (Abstract), (1987). Constancy of the ventricular interval was described in the aforementioned A. J. Camm et al. article and in the aforementioned U.S. Pat. No. 4,830,006 to Haluska et al.

U.S. Pat. No. 5,086,772 to D. J. Larnard et al., which issued on Feb. 11, 1992 and is entitled "Arrhythmia Control System Employing Arrhythmia Recognition Algorithm", describes a method for combining two simple morphological features with timing information to improve the rhythm discrimination process. This method considers first the rate, and uses the morphological information only in a special rate band, to classify individual heartbeats. The cardiac rhythm is then diagnosed on the basis of the classification of a number of successive heart beats. The Larnard et al. patent is assigned to the assignee of the present invention.

U.S. Pat. No. 5,000,189 to R. D. Throne et al., entitled "Method and System for Monitoring Electrocardiographic Signals and Detecting a Pathological Cardiac Arrhythmia Such as Ventricular Tachycardia" which issued on Mar. 19, 1991, is another example of the use of the shape or morphology of the intracardiac electrogram to achieve discrimination between ST and VT.

However, methods such as those used in Larnard et al. and in Throne et al. have been proven to be impractical for use in implantable cardioverter/defibrillators due to their high computational overhead. Implementation would require either excessive current drain to achieve the required computation by a conventional microprocessor, or specialized hardware that is undesirable because of cost, complexity and size.

U.S. patent application Ser. No. 07/875,161 filed Apr. 28, 1992 by D. Mason et al. and entitled "Apparatus and Method for Classifying Heart Rhythms Utilizing an Implantable Dual Chamber Cardioverter/Defibrillator", discloses a device utilizing electrograms from the atrium and the ventricle, a signal processing circuit for determining the times of atrial and ventricular events, and an algorithm for classifying the heart rhythm. This algorithm discriminates between different types of heart rhythms having overlapping ventricular rates and having similar atrial and ventricular rates, utilizing an analysis of the relationships between successive atrial and ventricular intervals (i.e., atrial-atrial, ventricular-ventricular, and atrial-ventricular). The Mason et al. application is assigned to the same assignee as the present invention.

The algorithm employed in Mason et al. classifies tachycardias, having similar atrial and ventricular rates and having ventricular-ventricular intervals which are less than a predetermined normal sinus interval, as pathological if such tachycardias:

1. have decreasing atrial-ventricular intervals which suddenly increase and then begin decreasing again; these are classified as slow dissociated ventricular tachycardias;

2. have successive increasing atrial-ventricular intervals which suddenly decrease and then begin increasing again; these are also classified as slow dissociated ventricular tachycardias;

3. have atrial-ventricular intervals which are significantly different from the atrial-ventricular intervals of a predetermined resting normal sinus rhythm; these are classified as ventricular tachycardias with a 1:1 retrograde;

4. have the difference between any two different selected atrial-ventricular intervals, in a predetermined number of consecutive atrial-ventricular intervals thereof greater than two, in excess of a predetermined value; these are classified as slow dissociated ventricular tachycardia; and 5. have their ventricular-ventricular intervals exceed a predetermined lower interval limit value and have their atrial-ventricular intervals significantly different from the atrial-ventricular intervals of a predetermined resting normal sinus rhythm; these are classified as ventricular tachycardias with a 1:1 retrograde.

Although the Mason et al. method distinguishes among physiological sinus tachycardia, pathological slow dissociated ventricular tachycardia, and pathological ventricular tachycardia with a 1:1 retrograde, based on the sequence and character of intervals between atrial and ventricular events, it cannot classify other heart rhythms, nor can it classify similar pathological rhythms that may have different manifestations than those listed above.

It is, therefore, a primary object of the present invention to provide an improved rhythm classification system for implantable dual chamber cardioverter/defibrillators.

It is a further object of the invention to provide, in an ICD, algorithms for implementing and linking together various of the aforementioned tests to produce a complete rhythm classification system.

Another object of the invention is to utilize a plurality of discriminators in combination in an ICD to provide an improved rhythm classification system.

Additional objects of the invention include the following: to significantly reduce the incidence of inappropriate therapy for ST; to reduce the need for beta-blockade as a standard management technique for patients with ST/VT rate overlap; to reduce inappropriate therapy in AF, which to a degree should remove current contra-indications of ICD therapy for patients who have AF; and to provide in an ICD the ability to confirm non-treatable tachycardias in a patient.

Further objects and advantages of the invention will become apparent as the following description proceeds.

SUMMARY OF THE INVENTION

Briefly stated, and in accordance with one embodiment of the invention, a plurality of discriminators are provided in an implantable ICD. An A/V interval ratio discriminator calculates the ratio of atrial intervals (A-A) to ventricular intervals (V-V). This ratio, which is expressed as a fraction, will be less than unity if the atria are beating faster than the ventricles, and greater than unity if the ventricles are beating faster than the atria.

Two thresholds are used to define three regions, as follows: (i) an A-dominant region, wherein the A/V interval ratio is less than unity; (ii) a V-dominant region, wherein the A/V interval ratio is greater than unity; and (iii) an intermediate region, where the A/V interval ratio is between the two thresholds.

When the A/V interval ratio is less than the A-dominant interval ratio threshold (i.e., in the A-dominant region), the atria are beating faster than the ventricles, and the rhythm is almost certainly AF or A-flutter. When the A/V interval ratio is greater than the V-dominant interval ratio threshold (i.e., in the V-dominant region), the ventricles are beating faster than the atria, and the rhythm is almost certainly VT or VF. When the A/V interval ratio is between the two thresholds (i.e., in the intermediate region), the atrial and ventricular rates are similar and the rhythm may be either ventricular or atrial in origin. In this case, the rhythm classifier utilizes one or more or a plurality of advanced rhythm discriminators selected from a group including a ventricular windowing discriminator, a ventricular interval variability discriminator, a sudden onset discriminator, and an AV delay creep discriminator, in combination with rate information and each other, to classify the rhythm.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

DESCRIPTION OF THE PREFERRED EMBODIMENTS

Figure 1:
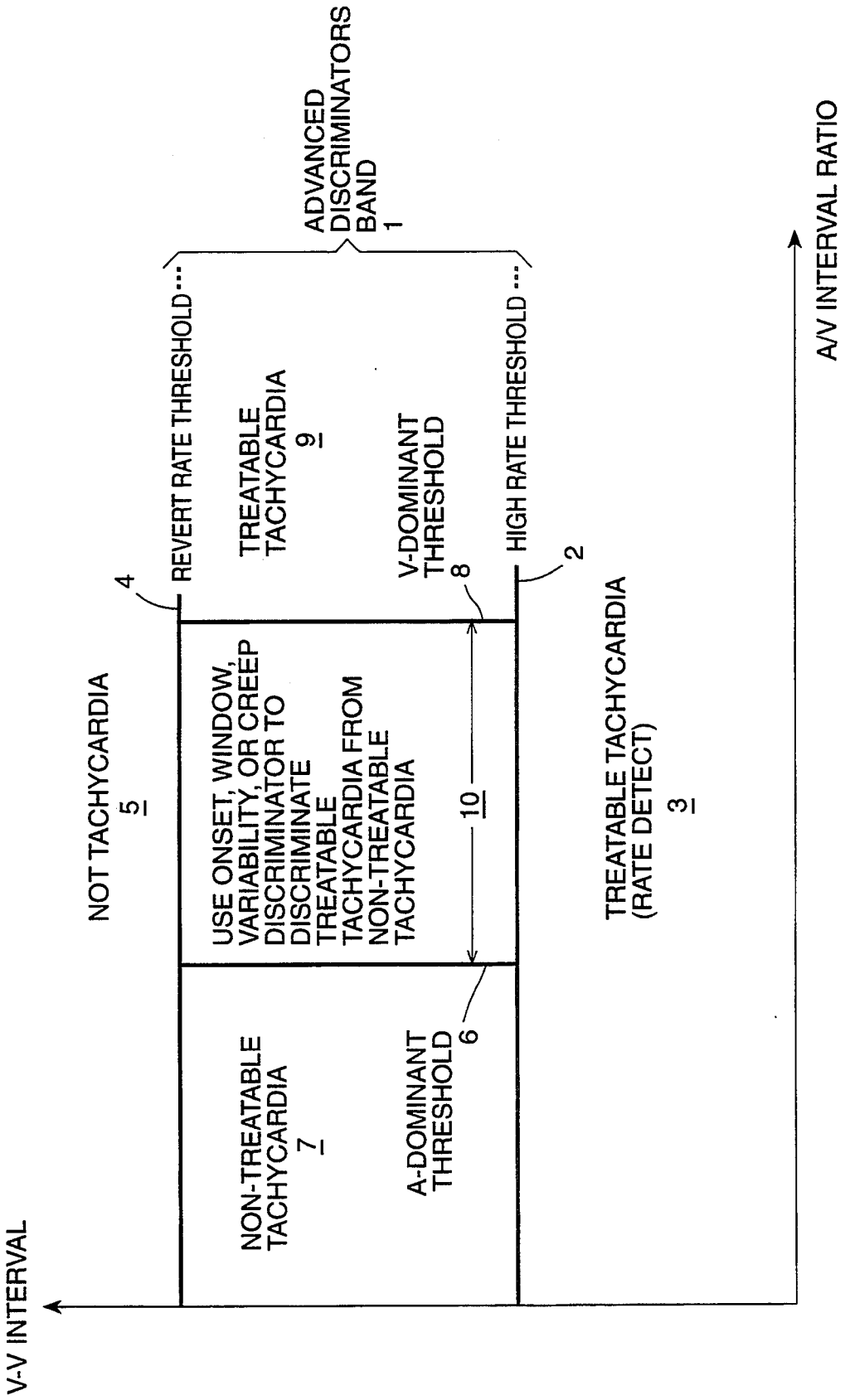
FIG. 1 is a diagrammatic view showing various discriminator outputs mapped into rhythm classifications in accordance with this invention.

In order to further clarify the invention, details are provided below with respect to the A/V interval ratio, ventricular windowing, ventricular interval variability, sudden onset and AV-delay creep discriminators, immediately below their respective headings. These discriminators would normally be implemented in software.

A/V Interval Ratio Discriminator

The A/V interval ratio discriminator or algorithm, briefly discussed earlier herein, calculates the ratio of atrial interval to ventricular interval. This ratio is expressed as a fraction.

Two thresholds, an A-dominant interval ratio threshold and a V-dominant interval ratio threshold, are used to define three regions. The A-dominant interval ratio threshold is a predetermined amount less than unity. When the AV interval ratio is less than the A-dominant interval ratio threshold, the atria are beating faster than the ventricles, and the rhythm is almost certainly AF or A-flutter. The V-dominant interval ratio threshold is a predetermined amount greater than unity. When the A/V interval ratio is greater than the V-dominant interval ratio threshold, the ventricles are beating faster than the atria, and the rhythm is almost certainly VT or VF. When the A/V interval ratio is between the two thresholds, the rhythm may be either ventricular or atrial in origin. In this case, it is known that the atrial and ventricular rates are similar, which information may be of use to the other discriminators. The three-region A/V interval ratio discriminator configuration is sometimes referred to herein as the "three-way interval ratio discriminator".

Alternatively, either the A-dominant interval ratio threshold or the V-dominant interval ratio threshold may be used individually to define two regions. Such two-region discriminator configurations are referred to herein as the A-dominant interval ratio discriminator and the V-dominant interval ratio discriminator, as the case may be.

The interval ratio may be calculated from a number of recent A-A intervals and V-V intervals. The average A-A interval could be calculated as the mean of the last 10 A-A intervals, for example. The average V-V interval would then be calculated as the mean of the last 10 V-V intervals. The interval ratio would then be the average A-A interval divided by the average V-V interval. In this document an interval ratio calculated in this way is referred to as follows: interval ratio (mean).

Alternatively, the interval ratio could be calculated as the ratio of medians, rather than means. The median is a special case of a rank-order calculation. The median A-A interval could be calculated as follows: take a list of the last 9 A-A intervals, for example, and place them in order from the smallest to the largest. The middle entry in the list (in this case the fifth entry) is the median A-A interval. The median V-V interval would similarly be calculated from an ordered list of the last 9 V-V intervals. The A-V interval ratio (rank) is then calculated as the median A-A interval divided by the median V-V interval.

Ventricular Windowing Discriminator

The ventricular windowing discriminator or algorithm is described in greater detail in the aforementioned U.S. patent application No. 07/875,161 to D. Mason et al. During normal sinus rhythm (NSR), the delay between atrial and ventricular depolarization is controlled by the delay in the AV node of the heart. This delay is fairly constant in a given patient, although it does tend to decrease in ST. Thus, after each atrial depolarization there is a "window" in which one would expect a ventricular depolarization to occur. The ventricular windowing discriminator works by counting the number of times that ventricular senses fall within this window. The window is defined by programmable offsets from the atrial sense.

If most ventricular senses fall in the window, then the A-V delay must be normal. Thus, the rhythm is most likely NSR or ST. In this manner, the ventricular windowing discriminator can differentiate between rhythm with normal (say ST) and abnormal (VT) AV delay, even when the atrial and ventricular rates are the same (for example, VT with 1:1 retrograde conduction). In fact, the discriminator is only intended to operate on rhythms that have similar atrial and ventricular rates, and so would normally be preceded by the A/V interval ratio discriminator. The name "ventricular windowing discriminator" will sometimes be abbreviated herein to just "window".

Ventricular Interval Variability Discriminator

During monomorphic VT, the ventricular intervals V-V are typically very stable. Conversely during AF, the ventricular intervals are typically very variable. One can thus use a measure of the beat-to-beat variability of ventricular intervals to help discriminate between AF and VT. This function is performed by the ventricular interval variability discriminator or algorithm. The variability of ventricular intervals during ST falls somewhere between that which occurs during AF and during VT, and tends to overlap both, so that the ventricular interval variability discriminator is not useful for identifying ST.

The name "ventricular interval variability discriminator" will sometimes be abbreviated herein to just "variability".

Sudden Onset Discriminator

Sinus tachycardia is the heart's normal response to exercise. The heart rate gradually increases to meet the increased requirement for blood flow. Ventricular tachycardia, on the other hand, is a fast pathological rhythm that can start without warning. The rate of increase of heart rate may be useful as a marker of VT. This measurement is performed by the sudden onset discriminator or algorithm. A fast rhythm with a sudden onset is likely to be VT, while a rhythm with a gradual onset is likely to be ST.

The name "sudden onset discriminator" will sometimes be abbreviated herein to just "onset".

AV-Delay Creep Discriminator

The A/V interval ratio test detects most VTs on the basis of the faster ventricular rate. When the atrial and ventricular rates are similar, however, it is unable to classify the rhythm.

If the atrial and ventricles are associated, then the AV-delay should be fairly consistent. It will have a degree of variability, but this will occur around some mean point. If on the other hand the atria and ventriculars are dissociated, then the AV-delay will tend to slowly decrease (assuming that the ventriculars are beating faster as in a VT).

Figure 4A:
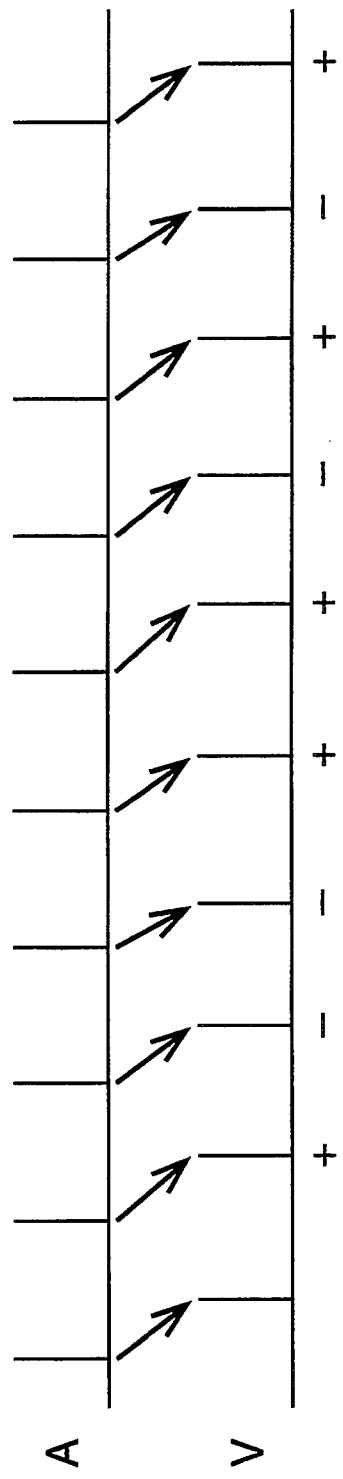
FIGS. 4A and 4B illustrate the operation of the AV-delay creep discriminator of the invention; and, FIG. 5 depicts a block diagram of an implantable cardiac device employing atrial and ventricular sensing leads and including a functional module for heart rhythm classification.
Figure 4B:
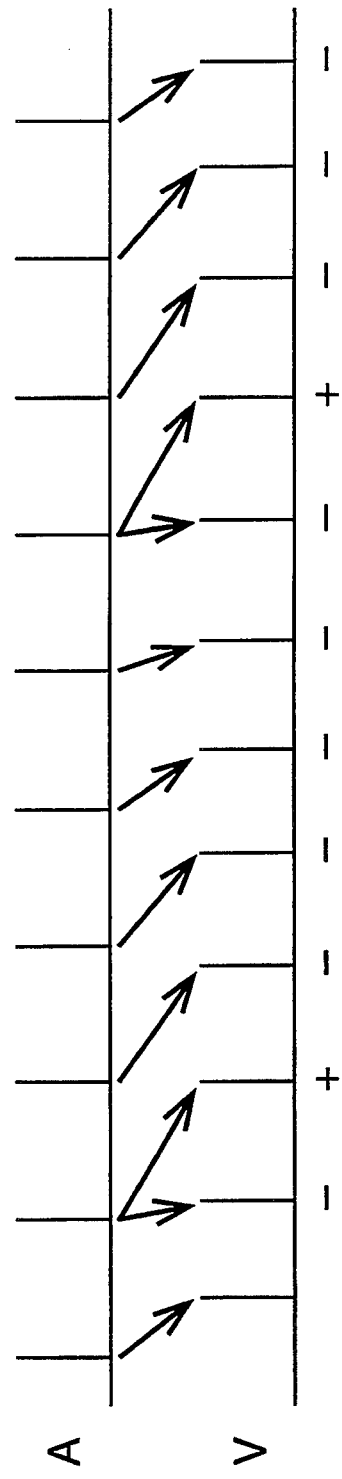

Referring to FIGS. 4A and 4B, the AV-delay creep discriminator or algorithm looks for this decreasing trend (or creep) in the AV-delay by checking the sign of the beat-to-beat difference in AV-delay. If there are similar numbers of positive and negative differences between successive AV-delays, as shown in FIG. 4A, this indicates a sinus tachycardia (ST). If most of the differences have the same sign, as shown in FIG. 4B, then the AV-delay is creeping in one direction. This indicates a dissociated rhythm, most likely VT.

The name "AV-delay creep discriminator" will sometimes be abbreviated herein to just "creep".

The rhythms with which a rhythm classifier according to the present invention must cope, and the preferred rhythm classification for each, is shown below in TABLE 1.

TABLE 1

| RHYTHM | RHYTHM CLASSIFICATION |
| --- | --- |
| Normal Sinus Rhythm (NSR) | Not Tachycardia |
| Sinus Tachycardia (ST) | Non-Treatable Tachycardia |
| Atrial Flutter/Fibrillation (A-Flutter, AF) | Non-Treatable Tachycardia |
| Ventricular Tachycardia (VT) | Treatable Tachycardia |
| Ventricular Fibrillation (VF) | Treatable Tachycardia |

Atrial defibrillation is characterized by a very high atrial rate. The A/V interval ratio test has proven very useful in classifying AF. The fact that the present invention can identify rhythm with a higher ventricular rate than atrial rate helps to ensure that VT sensitivity is not compromised.

Ventricular variability is also a useful discriminator for AF. In a dual chamber system, variability can be combined with A/V interval ratio. This assists to ensure that VTs with a variable ventricular rate are not misclassified as non-treatable tachycardia.

Sinus tachycardia can be addressed by either the ventricular windowing algorithm or the sudden onset algorithm. As is the case for AF, the use of the A/V interval ratio algorithm will screen out the majority of VTs on the basis of the higher ventricular rate. This should mean that the error rate of onset in combination with A/V interval ratio is acceptible, whereas onset alone (in a single chamber system) is less satisfactory. The ventricular windowing algorithm similarly gains improved VT sensitivity.

As indicated earlier, the detection rhythm classifier of the present invention makes use of a number of advanced rhythm discriminators. These comprise:

A/V interval ratio discriminator
Ventricular windowing discriminator
Ventricular interval variability discriminator
Sudden onset discriminator
AV-delay creep discriminator A system has been devised to use these advanced discriminators in combination with rate information and with each other. This system is based on a generic rate-band that is located between a revert rate interval and a high rate detect interval, and in which band a rhythm classification of either treatable tachycardia or non-treatable tachycardia is possible. This band is termed the advanced discriminators band. Within this band, A/V interval ratio is always applied.

Rhythms where the ratio of atrial to ventricular interval is greater than some threshold (the V-dominant threshold) are always classified as treatable tachycardia. (The atrial interval is numerically larger, which means that the ventricles are beating faster, hence the name V-dominant threshold. This is almost certainly VT, and so is classified as treatable tachycardia). Rhythms where the ratio of atrial to ventricular interval is less than some threshold (the A-dominant threshold) are always classified as non-treatable tachycardia. (The atrial interval is numerically smaller, which means that the atria are beating faster, hence the name A-dominant threshold. This is almost certainly AF or A-flutter, and so is classified as non-treatable tachycardia).

Rhythms where the ratio of atrial to ventricular interval is between the two thresholds are classified by an additional discriminator, the additional discriminator being any one of sudden onset, ventricular windowing, ventricular interval variability, or AV-delay creep. These discriminator outputs are mapped into rhythm classifications, as shown diagrammatically in FIG. 1 and in TABLE 2, below.

TABLE 2

| DISCRIMINATOR | OUTPUT | CLASSIFICATION |
| --- | --- | --- |
| A/V INTERVAL RATIO | A-Dominant | Non-treatable Tachycardia |
| A/V INTERVAL RATIO | V-Dominant | Treatable Tachycardia |
| A/V INTERVAL RATIO | Approximately 1:1 | Use Another Discriminator |
| ONSET | Gradual Onset | Non-treatable Tachycardia |
| ONSET | Sudden Onset | Treatable Tachycardia |
| WINDOW | Normal A-V Delay | Non-treatable Tachycardia |
| WINDOW | Abnormal A-V Delay | Treatable Tachycardia |
| VARIABILITY | Low Variability | Treatable Tachycardia |
| VARIABILITY | High Variability | Non-treatable Tachycardia |
| CREEP | Dissociated | Treatable Tachycardia |
| CREEP | Associated | Non-treatable Tachycardia |

Referring now to FIG. 1, a generic dual-chamber rhythm classifier configuration in accordance with one embodiment of the present invention has been diagrammatically illustrated. The A/V interval ratio, which increases in the direction of the arrow on the horizontal axis, is shown plotted against the V-V interval, which increases in the direction of the arrow on the vertical axis. As shown, short V-V intervals (i.e., those below a high rate threshold are classified as treatable tachycardias in a region 3, and long V-V intervals (i.e., those greater than a revert rate threshold 4) are classified as not tachycardia in a region 5. High rate threshold 2 and revert rate threshold 4 may have nominal values of 250 ms and 500 ms, respectively. High rate threshold 2 and revert rate threshold 4 delimit an advanced discriminators rate band 1 therebetween.

For V-V intervals between the high rate threshold 2 and the revert rate threshold 4 (i.e., within band 1), an A-dominant threshold 6 is formed for lower A/V interval ratios and a V-dominant threshold 8 is formed for higher A/V interval ratios. A-dominant threshold 6 and V-dominant threshold 8 may have nominal values of 0.7 and 1.3, respectively. Rhythms below the A-dominant threshold 6 are classified as non-treatable tachycardias in a region 7, while rhythms above the V-dominant threshold 8 are classified as treatable tachycardias in a region 9. Rhythms which lie in a middle region 10, between the two thresholds 6 and 8, are classified by another discriminator. The additional discriminator may be any one of the aforementioned sudden onset discriminator, ventricular windowing discriminator, ventricular interval variability discriminator or AV-delay creep discriminator.

The rhythm classification system of the present invention can be programmed in a number of ways. The interval thresholds 2 and 4, or the A- and V-dominant thresholds 6 and 8, or both sets of thresholds, which delimit middle region 10 of the the advanced discriminators rate band 1, could be set equal to each other. Thus, the advanced discriminators would be inactive. The system would then resemble a simple single chamber device. This is called the "standard" configuration.

Alternatively, the classification system can be programmed to any one of six preset detect configurations. These configurations have been identified as appropriate to particular patient conditions, and have demonstrated very little compromise to VT sensitivity on test data. The six configurations are shown below in TABLE 3, wherein the terms "non-TT and "TT" mean non-treatable tachycardia and treatable tachycardia, respectively, and the symbol " " denotes an A/V interval ratio boundary.

The V-dominant threshold of the three-way interval ratio discriminator (the right " " symbol in the Detect Configurations of TABLE 3) is designed to discriminate dissociated ventricular tachycardias from other rhythms. All configurations must make this distinction, so all include the V-dominant threshold.

The onset and window discriminators are designed to discriminate between sinus tachycardia and ventricular tachycardia. Thus they are available in configurations that must deal with sinus tachycardia (the ST and ST/AF configurations).

The A-dominant threshold of the three-way interval ratio discriminator (the left " " symbol in the Detect Configurations of TABLE 3) is designed to discriminate atrial fibrillation from other rhythms. Thus it is available in configurations that must deal with atrial fibrillation (the AF and ST/AF configurations).

The variability discriminator is unable to discriminate sinus tachycardia from other rhythms. It is designed specifically for atrial fibrillation. Thus it is available only in configurations that do not deal with sinus tachycardia (it is available for AF, but not ST or ST/AF).

TABLE 3

| RHYTHMS | DETECT CONFIGURATION | | | |
|---------|------|------|-------------|----|
| ST/AF   | Non-TT | Onset | TT        |    |
| ST/AF   | Non-TT | Window | TT       |    |
| ST      | Window | TT   |             |    |
| ST      | Onset  | TT   |             |    |
| AF      | Non-TT | Variability | TT   |    |
| AF      | Non-TT | TT   |             |    |

Additionally, the individual parameters of the classifier according to the present invention could be modified one by one to achieve any desired configuration. This would be a custom configuration. For example, one of the AF configurations shown in TABLE 3 is:

Non-TT : Variability : TT

The left hand threshold (A-dominant threshold) is nominally 0.7. It could be changed to zero, resulting in the custom configuration:

Variability : TT

In a further embodiment of the present invention, the dual chamber rhythm classifier configuration may be extended to include other rhythm discriminators in the middle region 10 of FIG. 1. These additional discriminators can discriminate on the basis of ventricular electrogram morphology, active sensing, minute ventilation, and right ventricular pressure.

Figure 2:
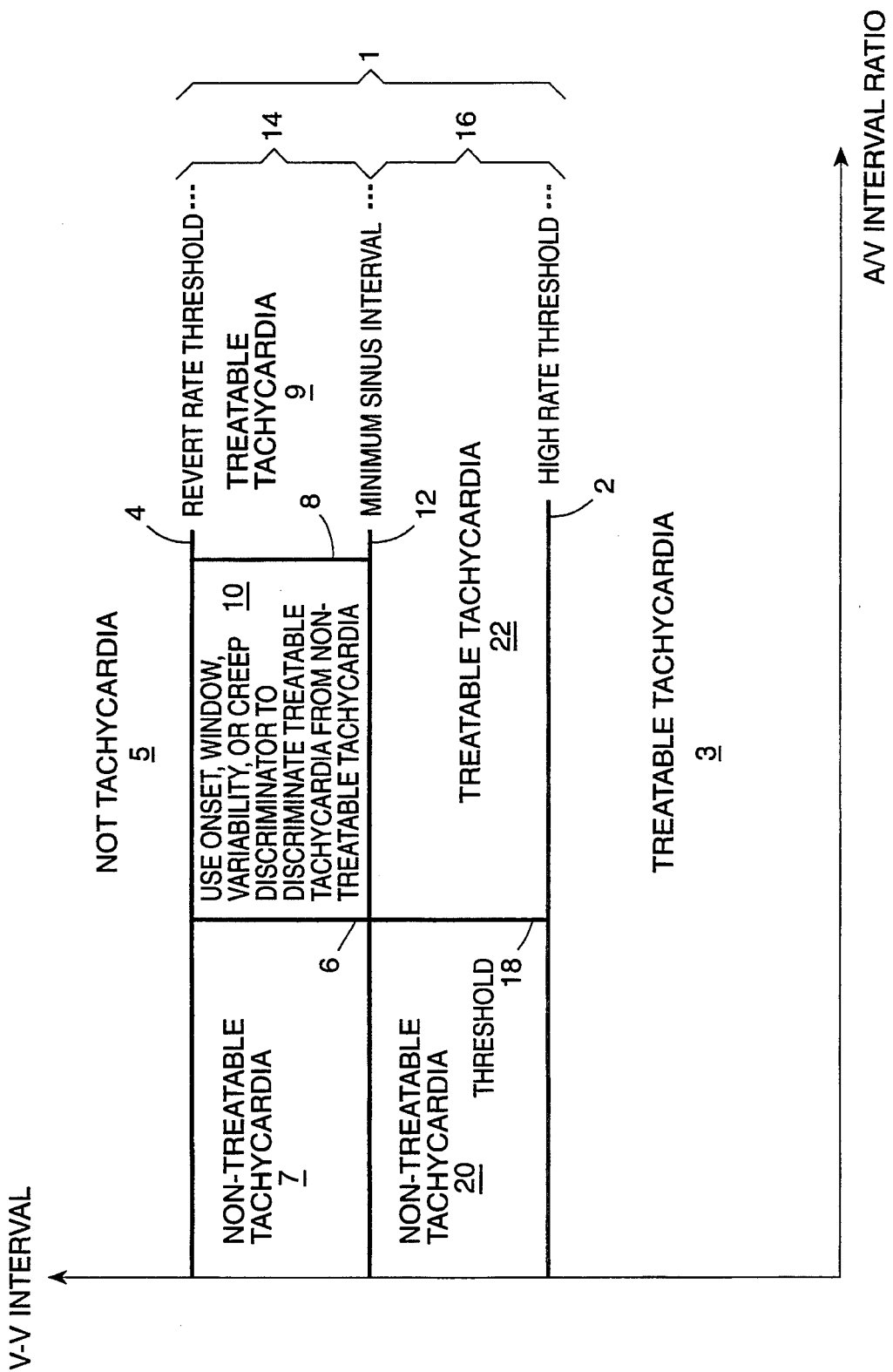
FIG. 2 is a diagrammatic view directed to an embodiment of the invention which utilizes a two-band classifier configuration.

Alternatively, or additionally, in other embodiments of the invention, the advanced discriminators rate band 1 can be split in two. Referring to FIG. 2, the patient's minimum sinus interval 12 may be used to form a boundary between a region 14, tailored to AF, and a region 16, tailored to ST. Minimum sinus interval 12 may have a nominal value of 350 ms.

The region 14, tailored to AF, includes the regions 7, 9 and 10, and the thresholds 6 and 8, previously discussed in connection with FIG. 1. Rhythms falling within region 14 are classified in the manner discussed earlier in connection with that figure. Rhythms which fall within the region 16, tailored to ST, are either treatable or non-treatable depending upon the relationship of their A/V interval ratio to a threshold 18, which divides the region 16 into a non-treatable tachycardia zone 20 and a treatable tachycardia zone 22. Threshold 18 may have a nominal value of 0.7.

It is to be understood that within the middle region 10 of FIGS. 1 and 2, the ICD may activate two or more advanced discriminators at the same time in classifying a given rhythm. This arrangement would constitute yet another embodiment of the present invention.

Figure 5:
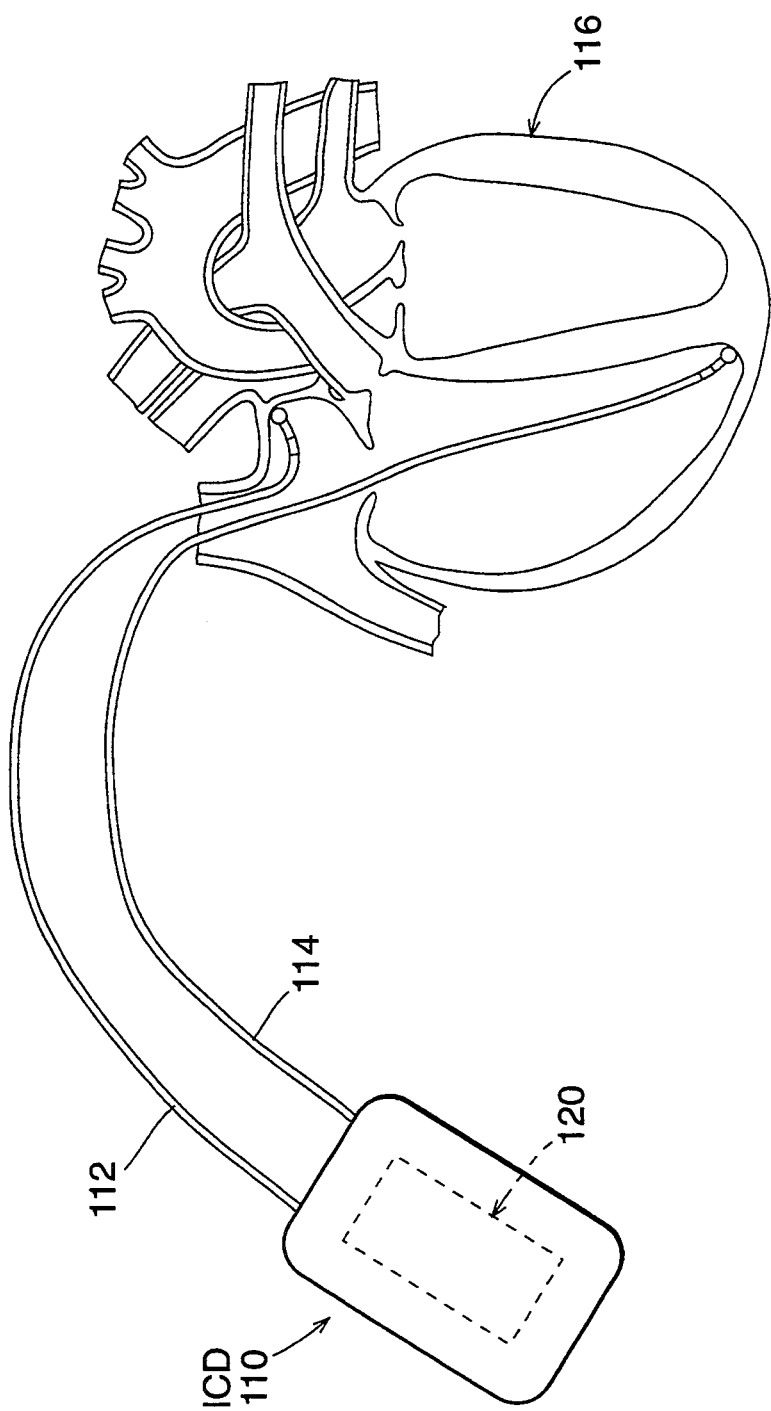

During implementation of the present invention within an ICD, for example the ICD 110 shown in FIG. 5, when an episode detector (not shown) is triggered, the device enters a tachycardia alert mode. A rhythm classification is made in the tachycardia alert mode using only A/V intervals that have occurred since the device entered the tachycardia alert mode. (Onset is an exception—it must operate on a window of A/V intervals that includes the onset of the arrhythmia).

The initial output of each discriminator should be "wait". As each of the discriminators accumulates the required number of A/V intervals, its output will change to one of the active outputs listed earlier in the middle column of TABLE 2.

While in the tachycardia alert mode, the rhythm classifier hierarchy is traversed on each ventricular beat. The next state of the device depends on the output of the classifier, as shown in TABLE 4 below.

TABLE 4

| CLASSIFIER OUTPUT | NEXT STATE |
|---|---|
| unavailable | Tachycardia Alert |
| Not Tachycardia | Monitor |
| Non-Treatable Tachycardia | Nil Therapy |
| Treatable Tachycardia | Antitachycardia Pacing (ATP) or Defibrillation Therapy |

Figure 3:
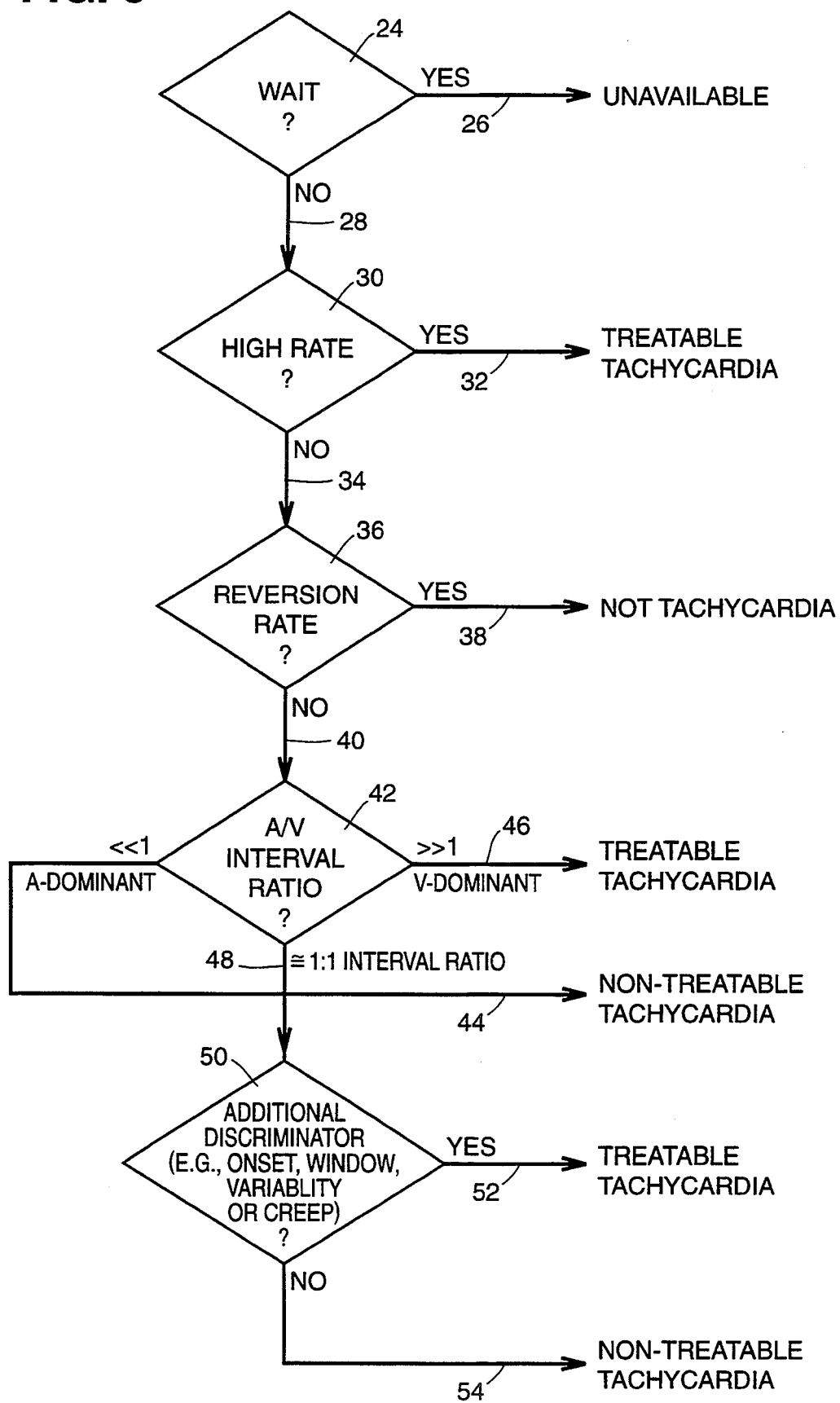
FIG. 3 shows a flowchart of the preferred embodiment of the invention.

The operation of the dual chamber rhythm classifier on each ventricular beat proceeds according to a hierarchy shown in FIG. 3, which figure comprises a flow chart of the process employed by the classifier. In this process the device looks at high rate, reversion rate, the A/V interval ratio and, if necessary, an additional discriminator in order to classify a heart rhythm.

Referring to FIG. 3, if the output at logic block 24 of a ventricular rate discriminator (not shown) is "wait", then a rhythm classification of "unavailable" results, as shown at 26. If the ventricular rate discriminator is no longer in the "wait" period, as shown at 28, a decision is made at a logic block 30 as to whether or not the output of the discriminator is at a high rate (i.e., is the V-V interval less than the high rate threshold 2 of FIG. 1).

If the output of the ventricular rate discriminator is at a high rate, then a rhythm classification of "treatable tachycardia" results, as shown at 32. If the ventricular rate discriminator output is not at a high rate, as shown at 34, a reversion rate discriminator (not shown) is interrogated next, as shown at logic block 36. If the reversion rate discriminator output is "reversion rate" (i.e., the V-V interval is greater than the revert rate threshold 4 of FIG. 1) than a rhythm classification of "not tachycardia" results, as shown at 38. If the reversion rate discriminator output is not at a reversion rate, as shown at 40, then the A/V interval ratio discriminator is interrogated next, as shown at logic block 42.

The discussion up to this point deals with the "detection" process of the rhythm classifier. This takes place when the heart rate first exceeds an episode detector threshold (not shown). When that occurs, the system must make an initial rhythm classification. If that rhythm classification is treatable tachycardia, then the device will enter a generic therapy sequence, and the advanced discriminators will have no further part to play. The primary concern in detection is to maximize VT sensitivity, since this directly relates to patient survival.

If the initial rhythm classification was of a non-treatable tachycardia, however, the device will enter a nil therapy mode. The advanced discriminators are only used for confirmation in the nil therapy mode.

In this mode, the device must continually confirm the presence of the non-treatable tachycardia. Since this will happen many times, the sensitivity of the device to non-treatable tachycardia is now of prime concern. This leads to a different trade-off in classifier parameters. A number of configurations have been devised which should provide suitable performance. The selection of the confirmation configuration is dependent on the detection configuration. The physician should only have limited flexibility in this regard. The proposed mapping between detection and confirmation configurations is shown in TABLE 5 below.

TABLE 5

| RHYTHMS | DETECT CONFIGURATIONS | CONFIRM CONFIGURATIONS |
|---------|----------------------|------------------------|
| ST/AF   | Non-TT : Onset : TT  | Non-TT : AV-Diff : TT  |
|         |                      | Non-TT : TT            |
| ST/AF   | Non-TT : Window : TT | Non-TT : Window : TT   |
|         |                      | Non-TT : AV-Diff : TT  |
|         |                      | Non-TT : TT            |
| ST      | Window : TT          | Window : TT            |
|         |                      | AV-Diff : TT           |
|         |                      | Non-TT : TT            |
| ST      | Onset : TT           | AV-Diff : TT           |
|         |                      | Non-TT : TT            |
| AF      | Non-TT : Variability : TT | Non-TT : Variability : TT |
|         |                      | Non-TT : TT            |
| AF      | Non-TT : TT          | Non-TT : TT            |
|         |                      | Non-TT : Variability : TT |

If the A/V interval ratio discriminator output is "wait" then a rhythm classification of "unavailable" (not shown) results, as before. If the output of this discriminator is "A-dominant" then a rhythm classification of "non-treatable tachycardia" results, as shown at 44. If the output of this discriminator is "V-dominant", then a rhythm classification of "treatable tachycardia" results, as shown at 46. If the output is "approximately 1:1 interval ratio" as shown at 48, then an additional discriminator (e.g., onset, ventricular windowing, ventricular variability or AV-delay creep) is interrogated, as shown at logic block 50.

If the output of the additional discriminator interrogated at logic block 50 is "wait", a rhythm classification of "unavailable" (not shown) results, as before. Otherwise, a rhythm classification of either "treatable tachycardia", as shown at 52, or "non-treatable tachycardia", as shown at 54, will result.

The maximum number of intervals that will be required for a rhythm classification to be made is equal to the maximum value programmed for any of the individual discriminators. Fast VT or VF would normally be classified by the ventricular rate discriminator, and so will take a smaller number of intervals.

TABLE 5, above, maps detect configurations into confirm configurations. In this table the following terms have the meanings indicated: "Non-TT" means non-treatable tachycardia; "TT" means treatable tachycardia; " " denotes an A/V interval ratio boundary.

The discriminator parameters are different in detection and confirmation. This is true even where the classifier configuration is unchanged.

The AV-delay creep discriminator, discussed earlier herein, and described in the aforementioned U.S. patent application Ser. No. 07/875,161 to Mason et al., is designed to look for creep in the AV-delay. In dissociated rhythms with similar atrial and ventricular rates, the AV-delay should decrease in a number of small steps, then return to a larger value in one step (assuming the ventricle is beating faster). The method utilized compares the length of successive AV-delays, and tests the hypothesis that the number of decreases in AV-delay is substantially larger than the number of increases. This can be seen from the C Code for the AV-delay creep algorithm shown below:

```
int sign_test(int* av_delay_list, int y, double threshold)
{
```

```
        int i;
        int shorter;
        for (i = 0, shorter = 0; i < y; i + +)
            if (av__delay__list[i] < av__delay__list[i + 1])
                + + shorter;
            else if (av__Cdelay__list[i] > av__delay__list[i + 1]))
                − − shorter;
        return ( shorter > y * threshold);
    }
```

Initial tests employing the AV-delay creep algorithm looked for a creep in either direction. However, ST performance was found to be improved by looking only for decreasing AV-delay creep. It was found that for rhythms with dissimilar atrial and ventricular rates (V-V faster than A-A), there would be a significant number of missed atrial senses due to the post V-sense atrial absolute refractory period. This would confound the AV-delay creep discriminator.

The atrial undersensing would also result in a reduction in the apparent atrial rate, however. This can easily be detected by the A/V interval ratio algorithm. AV-delay creep, combined with three-way interval ratio, worked well for all of the dissociated VTs in the test data set.

The A-dominant test works very well for AF, and is preferred for the preset AF configurations. The use of variability with rate ratio would be a second option, simply on the basis of complexity. It is more robust when there is a problem with atrial undersensing.

In the preferred embodiment of this invention, only two advanced discriminators are applied at any one time in an attempt to control the complexity of the system. The complexity of the system affects the cost of implementing the system, the confidence in the final implementation, and the physician's acceptance. It is possible, however, to use three or more advanced discriminators at any one time.

Referring to FIG. 5, there is depicted a block diagram of an implantable cardiac device 110 that employs the heart rhythm classification system of the present invention. The device 110 is connected via atrial and ventricular leads 112 and 114, respectively, to a patient's heart 116, for the sensing of atrial and ventricular events. Within the implantable cardiac device 110 is a functional module 120 for the classification of sensed heart rhythms in the manner discussed earlier herein.

It will be apparent from the foregoing discussion that the present invention provides an improved rhythm classification system for an implantable dual chamber cardioverter/defibrillator. In addition, the invention provides, in an ICD, algorithms for implementing and linking together various rhythm classification tests to produce a complete rhythm classification system, the ICD utilizing a plurality of discriminators in combination in connection therewith.

While particular embodiments of the invention have been shown and described, it will be obvious to those skilled in the art that various other changes and modifications may be made without departing from this invention in its broader aspects, and it is, therefore, aimed in the appended claims to cover all such changes and modifications as fall within the true spirit and scope of this invention.

What is claimed is:

1. A method for monitoring and classifying cardiac rhythms of a patient's heart, comprising the steps of:

sensing atrial and ventricular events of the heart;

timing A-A intervals between said atrial events and V-V intervals between said ventricular events;

determining A/V interval ratios which comprise ratios of said A-A intervals to said V-V intervals; and responsive to said sensed events, classifying said rhythms, said classifying step including the sub-steps of (i) providing a first threshold establishing a V-V interval level below which sensed heart rhythms are classified as treatable tachycardia, (ii) providing a second threshold above which sensed heart rhythms are classified as not tachycardia, said first and second thresholds defining therebetween a band of V-V intervals which includes heart rhythms that comprise both non-treatable tachycardias and treatable tachycardias, (iii) providing a third threshold in said band establishing an A/V ratio below which sensed heart rhythms have A-A intervals which are shorter than the V-V intervals thereof and are classified as non-treatable tachycardias, and (iv) providing a fourth threshold establishing an A/V interval ratio above which sensed heart rhythms have V-V intervals which are shorter than the A-A intervals thereof and are classified as treatable tachycardias, said third and fourth thresholds defining therebetween a middle region wherein said A-A intervals and said V-V intervals are approximately the same, said classifying step including a further sub-step, responsive to those heart rhythms that fall within said middle region, of discriminating further among said heart rhythms in said middle region in order to classify said rhythms into non-treatable tachycardias and treatable tachycardias.

2. A method according to claim 1, wherein said discriminating sub-step includes the further sub-step of using at least one discriminator, selected from a group including a ventricular windowing discriminator, a ventricular interval variability discriminator, a sudden onset discriminator, an AV-delay creep discriminator, a ventricular electrogram morphology discriminator, an active sensing discriminator, a minute ventilation discriminator and a right ventricular pressure discriminator, in order to classify said heart rhythms into non-treatable and treatable tachycardias.

3. A method according to claim 2, said method including the further step, responsive to classification of a heart rhythm that falls within said middle region as a non-treatable tachycardia, of utilizing a discriminator other than the discriminator used in said discriminating sub-step to confirm the classification of said heart rhythm as a non-treatable tachycardia.

4. A method according to any one of claims 1-3, wherein said classifying step includes the further sub-steps of (v) providing a fifth threshold and (vi) providing a sixth threshold, said fifth threshold being intermediate said first and second thresholds and comprising the patient's minimum sinus V-V interval, said fifth threshold and said first threshold defining an ST region therebetween, said sixth threshold establishing an A/V interval in said ST region below which heart rhythms are classified as non-treatable tachycardias and above which heart rhythms are classified as treatable tachycardias, said fifth threshold and said second threshold defining an AF region therebetween containing said third and fourth thresholds.

5. An implantable dual chamber cardioverter/defibrillator device for monitoring and classifying cardiac rhythms of a patient's heart, comprising:

means adapted to be coupled to the atrium and ventricle of the heart for sensing atrial and ventricular events thereof, said sensing means including means for timing A-A intervals between said atrial events and V-V intervals between said ventricular events, and said sensing means further including means for determining A/V interval ratios which comprise ratios of said A-A intervals to said V-V intervals;

means operatively connected to said sensing means and responsive thereto for classifying said rhythms, said classifying means including (i) a first threshold establishing a V-V interval level below which sensed heart rhythms are classified as treatable tachycardia, (ii) a second threshold level above which sensed heart rhythms are classified as not tachycardia, said first and second thresholds defining therebetween a band of V-V intervals which includes heart rhythms that comprise both non-treatable tachycardias and treatable tachycardias, (iii) a third threshold in said band establishing an A/V interval ratio below which sensed heart rhythms have A-A intervals which are shorter than the V-V intervals thereof and are classified as non-treatable tachycardias, and (iv) a fourth threshold establishing an A/V interval ratio above which sensed heart rhythms have V-V intervals which are shorter than the A-A intervals thereof and are classified as treatable tachycardias, said third and fourth thresholds defining therebetween a middle region wherein said A-A intervals and said V-V intervals are approximately the same, said classifying means further including discriminating means responsive to those heart rhythms that fall within said middle region for classifying said heart rhythms into non-treatable tachycardias and treatable tachycardias.

6. A device according to claim 5, wherein said discriminating means comprises at least one discriminator selected from a group including a ventricular windowing discriminator, a ventricular interval variability discriminator, a sudden onset discriminator, an AV-delay creep discriminator, a ventricular electrogram morphology discriminator, an active sensing discriminator, a minute ventilation discriminator and a right ventricular pressure discriminator.

7. A device according to claim 5, wherein said classifying means, responsive to classification of a heart rhythm that falls within said middle region as a non-treatable tachycardia, utilizes a discriminator other than the discriminator used to make said classification to confirm said classification.

8. A device according to any one of claims 5-7, wherein said classifying means includes (v) a fifth threshold and (vi) a sixth threshold, said fifth threshold being intermediate said first and second thresholds and comprising the patient's minimum sinus V-V interval, said fifth threshold and said first threshold defining an ST region therebetween, said sixth threshold establishing an A/V interval in said ST region below which heart rhythms are classified as non-treatable tachycardias and above which heart rhythms are classified as treatable tachycardias, said fifth threshold and said second threshold defining an AF region therebetween containing said third and fourth thresholds.

* * * * *